United States Patent [19]
Reinehr et al.

[11] Patent Number: 5,457,198
[45] Date of Patent: Oct. 10, 1995

[54] WATER-SOLUBLE TRIAZINE DERIVATIVES

[75] Inventors: Dieter Reinehr, Kandern, Germany; Jean-Pierre Bacher, Buschwiller, France; Manfred Rembold, Aesch, Switzerland

[73] Assignee: Ciba-Geigy Corporation, Ardsley, N.Y.

[21] Appl. No.: 220,301

[22] Filed: Mar. 30, 1994

[30] Foreign Application Priority Data

Apr. 2, 1993 [CH] Switzerland .................. 1021/93

[51] Int. Cl.$^6$ .................. C07D 251/52; C07D 403/12
[52] U.S. Cl. .................. 544/193.1; 544/193.2
[58] Field of Search .................. 544/193.1, 193.2

[56] References Cited

FOREIGN PATENT DOCUMENTS 0546993  6/1993  European Pat. Off. .

91/04987  4/1991  WIPO .

OTHER PUBLICATIONS

Houben–Weyl–Methoden der Organischen Chemie, X/1, 1280 (1971).

Synthesis, 11, 901 (1984).

Chem. Abst., vol. 105, #14 (1986) #116416.

*Primary Examiner*—John M. Ford
*Attorney, Agent, or Firm*—Kevin T. Mansfield

[57] ABSTRACT

Water-soluble triazine derivatives of the formula (1) are described. The compounds are representatives from the class of sterically hindered mines (HALS stabilizers). They are suitable for increasing the thermal and photochemical stability of dyed and undyed polygamies fibre materials.

8 Claims, No Drawings

WATER-SOLUBLE TRIAZINE DERIVATIVES

The present invention relates to water-soluble triazine derivatives, processes for preparing these compounds, a process for the photochemical and thermal stabilization of polygamide fibre materials and to the fibre material treated with the compounds according to the invention.

The water-soluble triazine derivatives have the general formula

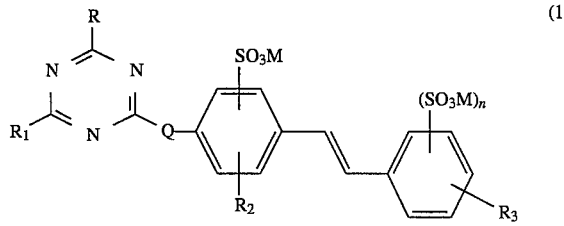

in which
R is a radical of the formula

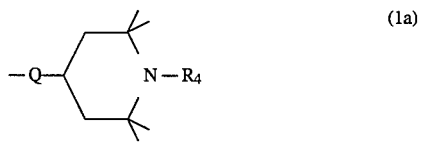

$R_1$ is halogen; lower alkyl; lower alkoxy; (lower alkyl)thio; mono(lower alkyl) amino; di(lower alkyl)amino; cycloalkoxy; cycloalkylthio; cycloalkylamino; sulfonated or unsulfonated phenyl, phenoxy, phenylamino, phenylthio, phenyl(lower alkoxy), phenyl(lower alkyl)amino or phenyl-(lower alkyl)thio; a radical of the formula

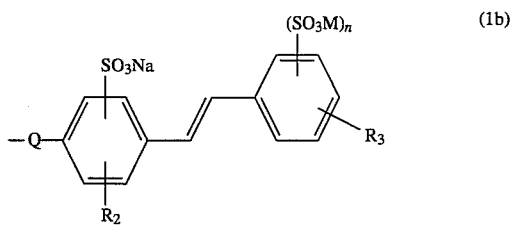

or a radical of the formula (1a), $R_2$ and $R_3$, independently of one another, are hydrogen, halogen, lower alkyl, lower alkoxy or a radical of the formula

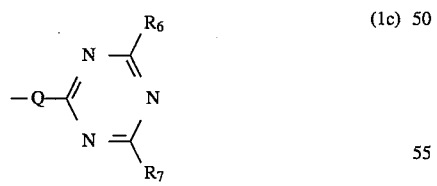

$R_4$ is hydrogen, oxyl, hydroxyl, lower alkyl, lower alkenyl, lower alkoxy, acyl or benzyl $R_5$ is hydrogen or lower alkyl, $R_6$ and $R_7$, independently of one another, are lower alkyl; lower alkoxy; (lower alkyl)thio; mono(lower alkyl)amino; di(lower alkyl)amino; sulfonated or unsulfonated phenyl, phenoxy, phenylamino, phenylthio, phenyl(lower alkoxy), phenyl(lower alkyl)amino or phenyl(lower alkyl)thio; or a radical of the formula (1a); M is hydrogen, an alkali metal, an alkaline earth metal, ammonium or an organic ammonium radical, Q is —O— or —($NR_5$)— and n is 0 or 1.

In the definition of the radicals $R_1$ to $R_7$, lower alkyl, lower alkoxy, (lower alkyl)thio, mono(lower alkyl)amino and di(lower alkyl)amino are groups or parts of groups containing 1 to 5, in particular 1 to 3, carbon atoms. Examples of such groups are methyl, ethyl, n-propyl, isopropyl, n-butyl, sec-butyl, tert-butyl, amyl or isoamyl or methoxy, ethoxy, isopropoxy, isobutoxy, tert-butoxy or tert-amyloxy or methylthio, ethylthio, propylthio or butylthio.

Lower alkenyl is, for example, vinyl, propenyl, butenyl or, preferably, allyl.

Phenyl(lower alkyl)amino is, for example, phenethyl-, phenylpropyl-, phenylbutyl- or, preferably, benzyl-amino.

In the radicals R and $R_2$, halogen is fluorine, bromine or, preferably, chlorine.

In the definition of the radical $R_4$, acyl is in particular formyl or lower alkanoyl, for example acetyl or propionyl, or benzoyl.

Examples of alkali metals are lithium, sodium or potassium. Sodium is preferred. Examples of alkaline earth metals are calcium and magnesium.

A suitable organic ammonium radical is trimethylammonium or, preferably, triethylammonium.

(Lower alkyl)amino, di(lower alkyl)amino and cyclo(lower alkyl)amino can be substituted by halogen, lower alkoxy, hydroxyl, carboxyl or carboxy(lower alkyl). Lower alkoxy and cycloalkoxy can be substituted by lower alkoxy. (Lower alkyl)thio and cycloalkylthio can be substituted by alkoxy or hydroxyl. Phenyl can be substituted by lower alkyl, lower alkoxy or halogen.

Of practical importance are those water-soluble triazine derivatives in which in formula (1) $R_1$ is halogen; lower alkoxy; (lower alkyl)thio; sulfonated or unsulfonated phenoxy, phenylamino, phenylthio; or a radical of the formula (1a).

Of these, triazine derivatives in which $R_1$ is a radical of the formula (1a) and triazine derivatives in which Q is —($NR_5$)— are of partiuclar interest.

Further important triazine derivatives of the formula (1) are those compounds in which $R_3$ is hydrogen or lower alkyl.

Also to the fore are triazine derivatives of the formula (1) in which $R_3$ is a radical of the formula (1c) and most especially those compounds in which in formula (1c) $R_6$ is hydrogen or lower alkyl.

Of particular interest are triazine derivatives of the formula (1) in which R and $R_1$ are a radical of the formula (1a), $R_4$ is hydrogen or lower alkyl, and n is 0.

The water-soluble triazine derivatives of the formula (1) can be prepared in various ways. In general, the starting compound is a 2,4,6-trihalo-s-triazine compound, preference being given to cyanuric chloride.

The triazine derivatives of the formula (1) according to the invention are prepared, for example, by reacting 1 mol of a 2,4,6-trihalo-s-triazine compound in succession with one or 2 mol of a stilbene compound of the formula

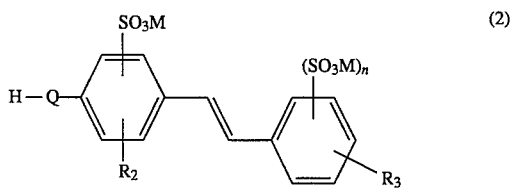

and 1 or 2 mol of the piperidine compound of the formula

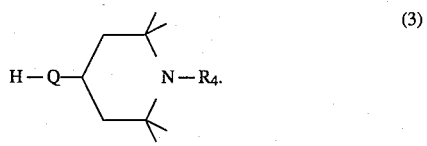

(3)

In these formulae $R_2$ and $R_3$, independently of one another, are hydrogen, lower alkyl and lower alkoxy. $R_4$, M, Q and n are as defined in formulae (1a) and (1b).

In the case where in formula (1b) $R_3$ is a radical of the formula (1c), the triazine derivatives of the formula (1) according to the invention are prepared by reacting 1 mol of the stilbene compound of the formula (2) in succession with 2 tool of a 2,4,6-trihalo-s-triazine compound and then with 4 mol of a piperidine compound of the formula (3) or with 2 mol of a pipeddine compound of the formula (3) and 2 mol of the corresponding mono(lower alkyl)amino, di(lower alkyl)amino, phenyl(lower alkyl)amino, phenoxy, phenylamino, lower alkoxy or (lower alkyl)thio compound.

The hydrohalic acid formed in the condensation reactions can be trapped by the end product itself or by adding a further base, for example aqueous ammonia, alkali metal hydroxides, alkali metal carbonates, alkali metal bicarbonates or of an organic base, for example triethylamine. Preferably, the base used is an alkali metal carbonate, for example sodium carbonate.

The reactions are advantageously carried out in aqueous solution, if desired with the addition of an aprotic organic solvent, for example acetone or methyl ethyl ketone. The starting 2,4,6-trihalo-s-triazine compounds are generally known. They are preferably used as aqueous suspensions. A particularly preferred starting compound is cyanuric chloride.

All compounds of the formula (1) are preferably used as sodium salts. To this end, they are dissolved, for example, in the equivalent amount of sodium hydroxide solution and formulated for an application as solution, dispersion or emulsion.

The novel compounds are representatives from the class of the sterically hindered amine stabilizers (HALS). They are suitable for increasing the thermal and photochemical stability of dyed and undyed polygamies fibre materials. Accordingly, the present invention also provides a process for the photochemical stabilization of polygamies fibre materials by means of these compounds. The process comprises treating the dyed or undyed polygamies fibre material with water-soluble triazine derivatives of the general formula

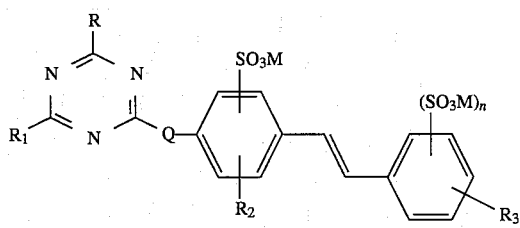

(1)

in which

R is a radical of the formula

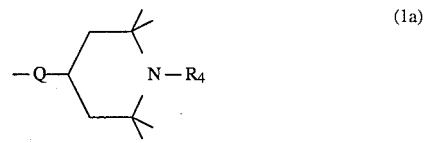

(1a)

$R_1$ is halogen; lower alkyl; lower alkoxy; (lower alkyl)thio; mono(lower alkyl) amino; di(lower alkyl)amino; cycloalkoxy; cycloalkylthio; cycloalkylamino; sulfonated or unsulfonated phenyl, phenoxy, phenylamino, phenylthio, phenyl(lower alkoxy), phenyl(lower alkyl)amino or phenyl(lower alkyl)thio; a radical of the formula

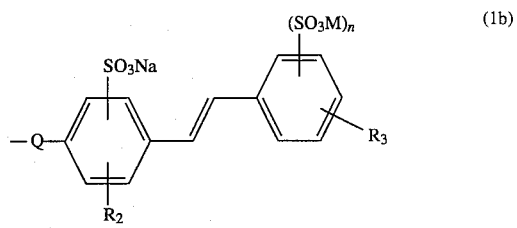

(1b)

or a radical of the formula (1a), $R_2$ and $R_3$, independently of one another, are hydrogen, halogen, lower alkyl, lower alkoxy or a radical of the formula

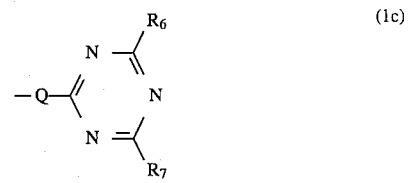

(1c)

$R_4$ is hydrogen, oxyl, hydroxyl, lower alkyl, lower alkenyl, lower alkoxy, acyl or benzyl $R_5$ is hydrogen or lower alkyl, $R_6$ and $R_7$, independently of one another, are lower alkyl; lower alkoxy; (lower alkyl)thio; mono(lower alkyl)amino; di(lower alkyl)amino; sulfonated or unsulfonated phenyl, phenoxy, phenylamino, phenylthio, phenyl(lower alkoxy), phenyl(lower alkyl)amino or phenyl(lower alkyl)thio; M is hydrogen, an alkali metal, an alkaline earth metal, ammonium or an organic ammonium radical, Q is —O— or —(NR$_5$)— and n is 0 or 1.

The compounds of the formula (1) can be applied to the polygamies fibre materials from customary liquors by common methods. According to the invention, they are applied from an aqueous bath containing the compounds in an amount of 0.005 to 10% by weight, preferably 0.05 to 2% by weight. The treatment with the compounds according to the invention and dyeing are preferably carried out in the same application bath. The procedure can be such that first the UV absorber is added to the aqueous application bath, the fibre material in question is treated, and then dyeing is carried out, or the UV absorber and the dye can be added simultaneously to the bath, or first dyeing can be carried out and then the treatment with the UV absorber can take place. Simultaneous application of UV absorber and dyes is preferred. Application can take place by the exhaust or continuous method.

In the exhaust method, the selected liquor ratio can be within a wide range, for example from 5:1 to 300:1, preferably 10:1 to 50:1. Application advantageously takes place at a temperature from 30° to 120° C., preferably 50° to 98° C.

In the continuous method, the amount of liquor applied is advantageously 30–400 % by weight, preferably 75–250% by weight. In order to fix the applied dyes and the known and novel compounds, the fibre material is subjected to a heat treatment. The fixation process can also take place by the cold pad-batch method.

The heat treatment preferably takes place by a steaming process in which treatment with steam which may be superheated takes place in a steamer at a temperature of 98° to 105° C for, for example, 1 to 7, preferably 1 to 5, minutes. Fixation of the dyestuffs and of the compounds of the formula (1) by the cold pad-batch method can be effected by storing the impregnated and, preferably, rolled-up goods at room temperature (15° to 30° C.) for, for example, 3 to 24 hours, this time being dependent, as is known, from the type of the dye applied.

After the dyeing process or fixation is complete, the treated fibre materials are rinsed and dried in the usual manner.

The process according to the invention provides not only polygamies dyeings but also polygamies fibres good thermal and photochemical stability.

Dyeings to be stabilized according to the invention include those produced by acid dyes or metal complex dyes, for example 1:2 chromium complex dyes, 1:2 cobalt complex dyes or copper complex dyes or disperse and reactive dyes.

Examples of such dyes are described in Colour Index, 3rd edition, 1971, volume 4.

Polygamies fibre material is understood to mean synthetic polygamies fibre material, for example nylon 6, nylon 6,6 or nylon 12, and modified polygamies, for example basic dyeable polygamies. Suitable fibre materials include, apart from the pure polygamies fibres, in particular polyurethane/polygamies fibre blends, for example, knitted fabric made of a 70:30 polygamies/polyurethane blend. Basically, the pure or blended polygamies fibre material can be present in a wide range of processing forms, for example as fibre, yarn, woven fabric, knitted fabric, nonwoven fabric or pile material.

The present process is suitable particularly advantageously for treating polygamies fibre material which is exposed to light and heat and is used, for example, as car upholstery fabric or carpet.

The examples which follow illustrate the invention. Pans and percentages are by weight.

PREPARATION EXAMPLES OF THE NOVEL COMPOUNDS

EXAMPLE 1

17 g of 4,4'-diaminostilbene-2,2'-disulfonic acid are dissolved in 100 ml of water, and the resulting solution is brought to a pH of 7.5 with 1 N sodium hydroxide solution. This solution is added drop wise at 0°–5° C. to a mixture of 18.4 g of cyanuric chloride, 200 ml of acetone and 10 g of ice while maintaining the pH at 2.5 to 3. After stirring at 5° C. for 2 hours, a solution of 17.6 g of metanilic acid is added drop wise, the pH is increased to 6.5 to 7, and the reaction mixture is stirred at 20° to 25° C. for another 2 hours. 31.2 g of 4-amino-2,2,6,6-tetramethylpiperidine are then added, the temperature is increased to 50° C. and the pH to 10–11, and the reaction mixture is stirred at 50° C. for 2 hours. The light brown solution is then evaporated, and the crude product obtained is recrystallized twice from water to give 56 g (88% of theory) of the light beige compound of the formula

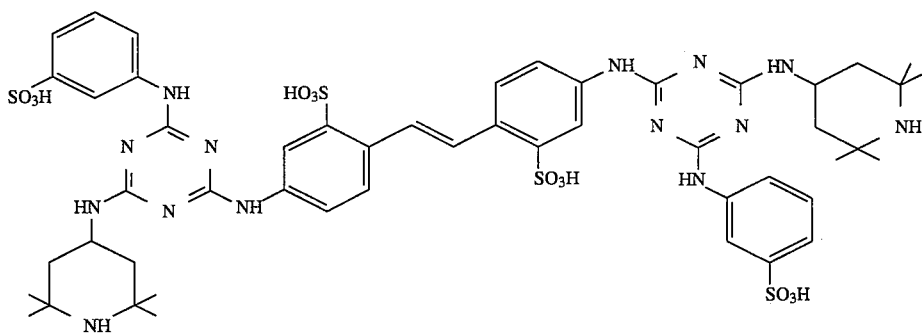

(101)

Absorption maximum: $\lambda_{max}$ 354 nm (measured in acetonitrile)

EXAMPLES 2 AND 3

The following compounds of the general formula (A) are prepared by the method described in Example 1:

| Compound | $R_1$ | $R_2$ | Yield | UV ($\lambda_{max}$) |
|---|---|---|---|---|
| (102) | —HN—⟨cyclohexyl(CH₃)₂⟩—NH— | —HN—⟨cyclohexyl(CH₃)₂⟩—NH— | 32% | 352 nm *) |
| (103) | —HN—⟨cyclohexyl(CH₃)₂⟩—NH— | —HN—C₆H₅ | 64% | 354 nm *) |

*) (measured in acetonitrile)

EXAMPLES 4 TO 6

The compounds of the general formula (B) are prepared by the method described in Example 1:

| Compound | R' | Yield | UV ($\lambda_{max}$) |
|---|---|---|---|
| (104) | —HN—⟨cyclohexyl(CH₃)₂⟩—NH— | 30% | 334 nm *) |
| (105) | —HN—C₆H₅ | 37% | 336 nm *) |
| (106) | —NH—(2-SO₃H-stilbenyl) | 38% | 343 nm *) |

*) (measured in acetonitrile)

Use Examples

EXAMPLE 7

3 specimens of 10 g each of nylon 6 knitwear (Lilion Texturtricot 5-4003) are dyed in a dyeing apparatus, for example Vistacolor from Zeller, at a liquor ratio of 25:1. The 3 baths additionally contain the following additaments: 1 g/l of sodium phosphate in a ratio of 25 parts of monosodium salt to 175 parts of disodium salt (pH 7.5), 1%, relative to the textile material, of a nonionic levelling agent.

While liquor 1 does not contain any further additives, 1% each, relative to the textile material, of the compounds of the formula (104) and (105) is added to liquors 2 and 3.

The liquors thus prepared are entered at 45° C. and heated to 95° C. over a period of 45 minutes. After a dyeing time of 40 minutes at 95° C., the liquor is cooled to 60° C., the fabric is rinsed with cold water, centrifuged and dried at room temperature.

The specimens thus treated are exposed to light in accordance with DIN 75.202 (FAKRA), and their breaking strengths are measured by SN (Swiss Norm) 198461. The results are shown in Table 1:

TABLE 1

| Addition to dyebath | Breaking strength after 120 hours exposure to FAKRA light in % |
|---|---|
| no addition | 10 |
| 1% of compound (104) | 71 |
| 1% of compound (105) | 63 |
| 1% of compound (106) | 56 |

3 further specimens treated in accordance with Example 1 are subjected to a heating test. It consists in ageing the specimens in a through-circulation oven at 140° C. for 72 hours, after which the breaking strength is determined by SN 198.461. The results are shown in Table 2:

TABLE 2

| Addition to dyebath | Breaking strength after 72 hours at 140° C. in % |
|---|---|
| no addition | 16 |
| 1% of compound (104) degree of exhaustion 94% | 43 |
| 1% of compound (105) degree of exhaustion 90% | 25 |
| 1% of compound (106) degree of exhaustion 71% | 23 |

The knitted fabrics treated with the compounds according to the invention exhibit distinctly higher breaking strengths not only under photochemical but also under thermal stress.

What is claimed is:

1. A water-soluble triazine derivative of the formula

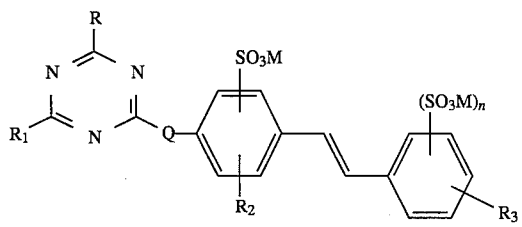

in which

R is a radical of the formula

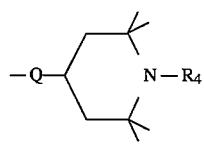

$R_1$ is halogen; lower alkyl; lower alkoxy; (lower alkyl)thio; mono(lower alkyl) amino; di(lower alkyl)amino; cycloalkoxy; cycloalkylthio; cycloalkylamino; sulfonated or unsulfonated phenyl, phenoxy, phenylamino, phenylthio, phenyl(lower alkoxy), phenyl(lower alkyl)amino or phenyl(lower alkyl)thio; a radical of the formula

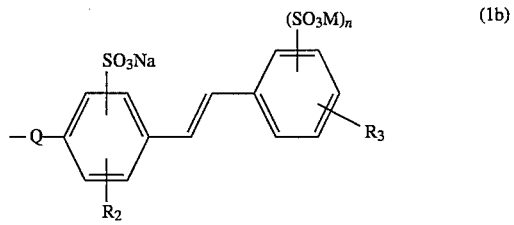

or a radical of the formula (1a) , $R_2$ and $R_3$, independently of one another, are hydrogen, halogen, lower alkyl, lower alkoxy or a radical of the formula

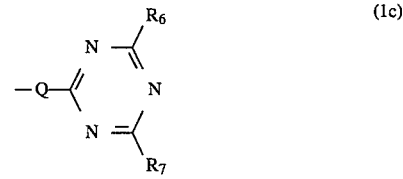

$R_4$ is hydrogen, oxyl, hydroxyl, lower alkyl, lower alkenyl, lower alkoxy, acyl or benzyl $R_5$ is hydrogen or lower alkyl, $R_6$ and $R_7$, independently of one another, are lower alkyl; lower alkoxy; (lower alkyl)thio; mono(lower alkyl)amino; di(lower alkyl)amino; sulfonated or unsulfonated phenyl, phenoxy, phenylamino, phenylthio, phenyl(lower alkoxy), phenyl(lower alkyl)amino or phenyl(lower alkyl)thio or a radical of the formula (1a); M is hydrogen, an alkali metal, an alkaline earth metal, ammonium or an organic ammonium radical, Q is —O— or —(NR$_5$)— and n is 0 or 1.

2. A triazine derivative according to claim 1, wherein $R_1$ is halogen; lower alkoxy; (lower alkyl)thio; sulfonated or unsulfonated phenoxy, phenylamino, phenylthio; or a radical of the formula (1a).

3. A triazine derivative according to claim 1, wherein $R_1$ is a radical of the formula (1a).

4. A triazine derivative according to claim 1, wherein Q is —(NR$_5$)—.

5. A triazine derivative according to claim 1, wherein $R_3$ is hydrogen or lower alkyl.

6. A triazine derivative according to claim 1, wherein $R_3$ is a radical of the formula (1c).

7. A triazine derivative according to claim 6, wherein in formula (1c) $R_6$ is hydrogen or lower alkyl.

8. A triazine derivative according to claim 1, wherein R and $R_1$ are a radical of the formula (1a), $R_4$ is hydrogen or lower alkyl, and n is 0.

* * * * *